United States Patent [19]

Travis

[11] Patent Number: 4,676,931

[45] Date of Patent: Jun. 30, 1987

[54] DIAGNOSTIC TEST REAGENTS AND METHOD FOR TESTING LIQUID PETROLEUM FUELS

[76] Inventor: Basil B. Travis, P.O. Box 287, Lodi, Calif. 95241

[21] Appl. No.: 799,351

[22] Filed: Nov. 18, 1985

[51] Int. Cl.$^4$ .............................................. G01N 31/00
[52] U.S. Cl. .................................... 252/408.1; 422/61
[58] Field of Search ...................... 252/408.1, 960, 964; 436/8, 19, 3, 39, 40, 60, 139, 143; 422/55, 61

[56] References Cited

U.S. PATENT DOCUMENTS 3,006,861 10/1961 Browning et al. ............... 252/408.1
4,608,345 8/1986 Feldman et al. ................. 252/408.1
4,615,828 10/1986 Wegrzyn .......................... 252/408.1

*Primary Examiner*—Deborah L. Kyle
*Assistant Examiner*—T. J. Wallen

[57] ABSTRACT

A composition of matter comprising three chemical reagents in combination with a three-step micro extraction method for testing flammability, oil and moisture content of liquid petroleum fuels.

1 Claim, No Drawings

DIAGNOSTIC TEST REAGENTS AND METHOD FOR TESTING LIQUID PETROLEUM FUELS

BACKGROUND OF THE INVENTION

This invention relates to a composition of matter for chemical diagnostic testing of liquid petroleum fuels under actual field conditions. More particularly, this invention relates to a method by which certain chemical reagents may be used in conjunction with liquid petroleum fuels to produce colors which are characteristic of fuel power, oil content and moisture content of liquid petroleum fuels.

The primary object of this invention is to provide a novel and relatively simple combination of chemical reagents to test unknown liquid petroleum fuels for power, oil and moisture content.

It is another object of this invention to provide a novel and relatively simple method by which said chemical reagents may be utilized in a test kit form.

These and other advantages will become apparent from the detailed disclosure of the present invention presented hereinafter.

As it is perhaps well known, liquid petroleum fuels are widely used in internal combustion engines, including marine and aircraft engines, and there are numerous kinds of petroleum fuels, each specifically formulated for a particular use. Since many of these fuels are not interchangeable, nor can they be distinguished by visual examination, the identification of a particular fuel composition is very important, especially where several different kinds of fuels are used for a variety of fueling operations. Along with the problem of identification, there is a lesser but related problem of contamination of fuels by oil and water which will also affect their performance. Currently, testing of fuels requires sophisticated laboratory analysis. It has been long felt that field tests, such as color tests, were needed for on the spot identification of fuels and detection of oil and water content because, more often than not, there is a long period between the laboratory analysis and actual fuel useage where changes in fuel chemistry or misidentification may occur during storage. Therefore, a simple field test may not only insure fuel integrity, but may also prevent a disaster due to human error or contamination.

Reliability, simplicity and ease of operation are three desirable characteristics for chemical field tests. They should be useable under a variety of adverse weather and environmental conditions, yet should pose no hazard to the person conducting the test nor to the environment. They should be fast, yet reproducible, and moreover be easily interpreted by non-technical personnel who may be required to test fuels during fueling operations. The above objectives among others are achieved by using three specially formulated chemical reagents according to the methods herein described.

SUMMARY OF THE INVENTION

A three-step method has been invented using three different chemical reagents to test fuel properties and, thus, determine the suitability of fuels for their intended use.

In Step One, the hydrocarbon composition of the liquid petroleum fuel is tested by its ability to extract free iodine from an iodine-triiodide solution.

In Step Two, the oil content of the liquid petroleum fuel is tested by its ability to extract Alizarin Red-S dye from an acetic acid solution of the dye.

In Step Three, the water content of the liquid petroleum fuel is tested by the ability of anhydrous cupric sulfate powder to extract moisture from the fuel.

In each of the above steps, the extraction may be carried out in a small glass vial where the resulting colors can be easily seen and may be compared to a color chart or other reference material.

DESCRIPTION OF THE PREFERRED EMBODIMENTS

This method generally tests a liquid petroleum fuel for aromatic and short chained hydrocarbons, oil (longer chained hydrocarbons), and moisture using three compositions of matter, each according to a particular step, and each step comprising an extraction with a preferred composition of matter and subsequent color observation.

Step One

In Step One, the preferred composition of matter is an iodinetriiodide reagent composed of 0.3% potassium iodide plus 0.1% iodine in distilled water. This reagent is indefinitely stable when kept in a tightly closed dark glass bottle. In this step, the preferred method of testing is performed in a one-dram clear glass vial with screw cap. Approximately 3 cc's of the iodine reagent is added to the vial and then approximately 1½ cc of fuel is also added. The cap is securely placed on the vial and it is shaken for about 5 seconds. The layers are allowed to separate and the color of the top layer (fuel) is visually examined immediately for the intensity of a red color.

It has generally been observed that higher numbered octane fuels, e.g. ethyl and aviation gasolines, will produce a bright red color while lower numbered octane fuels, e.g. diesel and kerosene fuels, will produce a dull red color. Fuels high in aromatics will cause bright red colors while fuels containing oils will cause dull red colors. Where excessive oil is present the color will be brown, as is observed with two-cycle engine fuels where oil is intentionally added. The general rule is that the more flammable, the brighter the red color. Thus, it is now possible to quite rapidly classify a particular fuel by use of a very simple test. A series of color charts may be helpful, but it has been observed by actual testing that the difference in colors are quite readily distinguished without the aid of a chart. However, because iodine itself is an oxidizer, the red color is not stable and will disappear with time. Therefore, color observation should be made within the first minute after extraction.

It should also be pointed out that although the preferred embodiment calls for a ratio of 2:1 iodine reagent to fuel for optimum color production, the method will also work for other ratios because the principle of the invention is the same. So too may the concentration of iodine reagent be varied to a degree without affecting the results. However, the iodine available for extraction must always be in excess as shown by the yellow color in the lower layer of the test vial solution. If the lower layer is clear after the test, too much fuel was used and the test should be repeated with less fuel. For example, the ideal test result for an aviation gasoline is a cherry red top layer over a yellow lower layer in the test vial solution.

Step Two

In Step Two, the preferred composition of matter is 1 mg per ml Alizarin Red-S dye in 10% aqueous acetic acid. This dye solution is indefinitely stable and may be stored in plastic dropping bottles. In this step, the preferred method of testing is also performed in a one-dram clear glass vial with screw cap. Approximately 10 drops of the dye solution are added to approximately 1½ cc of fuel in a test vial. The cap is securely placed on the vial and the vial is shaken for about 5 seconds. The layers are allowed to separate and the color in the top layer (fuel) is visually examined. If no oil is present, the color of the fuel will be unchanged. If oil is present, the color of the fuel will appear brown, the intensity of which is proportional to the amount of oil in the fuel.

The colors produced in test Step Two are indefinitely stable so that immediate observation is unnecessary and a series of known fuel samples can be made up in test vials with the dye solution for color comparison in lieu of a color chart. The ideal test result with an oil free fuel is clear over yellow, assuming of course that the fuel itself is clear. In practice, however, most liquid petroleum fuels are yellowish in color so that the actual observed test result is yellow over yellow (no change) for an oil free fuel. Where two-cycle engine fuels are tested, the fuel layer becomes distinctly brown, as for a 50:1 gasoline to oil ratio, and becomes dark purple when the oil content exceeds about 5%. It has been shown by experiment that a difference as small as 1% oil in fuel can be distinguished with this test.

Thus, it can be seen that Step Two is interrelated to Step One, because Step Two may be used as a confirmation test for oil. For example, where the iodine solution test of Step One would, perhaps, be unable to distinguish, say, two-cycle engine fuel from diesel fuel because of similar colors, Step Two would make this distinction by detecting oil in one fuel but not the other.

Step Three

In Step Three, the preferred composition of matter is anhydrous cupric sulfate powder. This powder is indefinitely stable if kept in a tightly closed container free of moisture. In this Step, the preferred method of testing is performed in a dry one-dram clear glass vial with screw cap. Approximately 50 milligrams of the anydrous powder is added to a test vial and then approximately 1½ cc of fuel is also added. The cap is securely placed on the vial and it is shaken for about 5 seconds. The powder is allowed to settle to the bottom of the vial and the powder is visually examined for a blue color.

Where there is no moisture in the fuel, the color of the powder will be unchanged. A small amount of moisture will turn the powder light blue and an excessive amount of moisture will cause the powder to appear dark blue. Since the color of the powder is indefinitely stable, immediate observation is unnecessary and a series of fuels with known moisture content can be made up with the anhydrous powder as standards for color comparisons.

It should also be pointed out that although there are several other known anhydrous powders which form insoluble colored salts in petroleum fuels, cupric sulfate was chosen as the perferred composition of matter for several reasons. First, it is relatively non-toxic in 50 milligram quantities which may be disposed of in a sanitary sewer or with refuse after a test. Secondly, it is inexpensive and readily available. Third, the anhydrous powder forms two hydrates. The monohydrate is light blue while the pentahydrate is dark blue. Thus, it can be seen that the intensity of the blue color is proportional to the amount of water available to the anhydrous powder by the fuel. In addition, the pentahydrate may be easily dried to anhydrous powder (colorless) by merely heating at 110° C. Therefore, if the powder should accidently become wet, it can be dried by even non-technical personnel.

While my invention has been described by means of specific examples and in a specific embodiment, I do not wish to be limited thereto, for obvious modifications will occur to those skilled in the art without departing from the spirit and scope of the invention.

I claim:
1. Kit for testing liquid petroleum fuels, said kit comprising:
   (a) about 0.3% potassium iodide plus 0.1% iodine in distilled water;
   (b) about 1 mg per ml of Alizarin Red-S dye in about 10% aqueous acetic acid;
   (c) anhydrous cupric sulfate powder.

* * * * *